United States Patent

Shorter et al.

[11] Patent Number: 5,116,383
[45] Date of Patent: May 26, 1992

[54] LOWELIMB PROTHESIS

[75] Inventors: John J. Shorter, Basing; Graham J. Harris, Basingstoke; Victor J. Woolnough, North Waltham, all of England

[73] Assignee: Chas. A. Blatchford & Sons Ltd., Hampshire, England

[21] Appl. No.: 318,917

[22] Filed: Mar. 3, 1989

[30] Foreign Application Priority Data

Mar. 4, 1988 [GB] United Kingdom ............... 8805191
Dec. 23, 1988 [GB] United Kingdom ............... 8830149

[51] Int. Cl.$^5$ .............................................. A61F 2/66
[52] U.S. Cl. .................................. 623/49; 623/50; 623/53; 623/55
[58] Field of Search .................... 623/53-56, 623/48, 49, 50-52, 47

[56] References Cited

U.S. PATENT DOCUMENTS

| | | | |
|---|---|---|---|
| 1,112,819 | 10/1914 | McFarland | 623/52 X |
| 4,461,045 | 7/1984 | Shorter et al. | 623/47 |
| 4,499,613 | 2/1985 | Yarrow | 623/48 |
| 4,645,508 | 2/1987 | Shorter | 623/48 |
| 4,645,509 | 2/1987 | Poggi et al. | 623/55 |
| 4,652,266 | 3/1987 | Truesdell | 623/55 |

FOREIGN PATENT DOCUMENTS

| | | | |
|---|---|---|---|
| 325171 | 10/1920 | Fed. Rep. of Germany | |
| 0800547 | 1/1936 | France | 623/52 |
| 1424831 | 9/1988 | U.S.S.R. | 623/55 |
| 738845 | 10/1955 | United Kingdom | |
| 852362 | 10/1960 | United Kingdom | |
| 1434413 | 5/1976 | United Kingdom | |
| 2008410 | 6/1979 | United Kingdom | |
| 2092451 | 8/1982 | United Kingdom | 623/47 |
| 2110936 | 6/1983 | United Kingdom | 623/49 |
| 2161390 | 1/1986 | United Kingdom | 623/48 |
| 2163961 | 12/1986 | United Kingdom | |
| 8800815 | 2/1988 | World Int. Prop. O. | 623/55 |

Primary Examiner—Randall L. Green
Assistant Examiner—David H. Willse
Attorney, Agent, or Firm—Hale and Dorr

[57] ABSTRACT

In a lower limb prothesis an energy storing foot (10) is combined with a resilient ankle joint (13) which is arranged to allow plantar flexion but substantially to prevent dorsi-flexion. The ankle joint (13) comprises a ball and socket joint (42). the socket (44) of which is extended downwardly on the anterior. medial and lateral sides to form a skirt (44A) positioned so as to compress a resilient ring (54) encircling a ball member (46) of the ball and socket joint (42). Metal plates (56) are embedded in the anterior part of the ring to prevent significant dorsi-flexion. The foot (10) has a single-piece carbon fiber reinforced plastics keel (12) having a lower spring portion (12B) connected at its posterior end as a cantilever to an upper ankle mounting portion (12). The resilient of the foot (10) is adjustable by means of a transversely extending support bar (28) which can be moved longitudinally by rotating an adjusting screw (30). The screw (30) passes through an aperture in the keel (12) and is accessible at the rear of the heel.

27 Claims, 3 Drawing Sheets

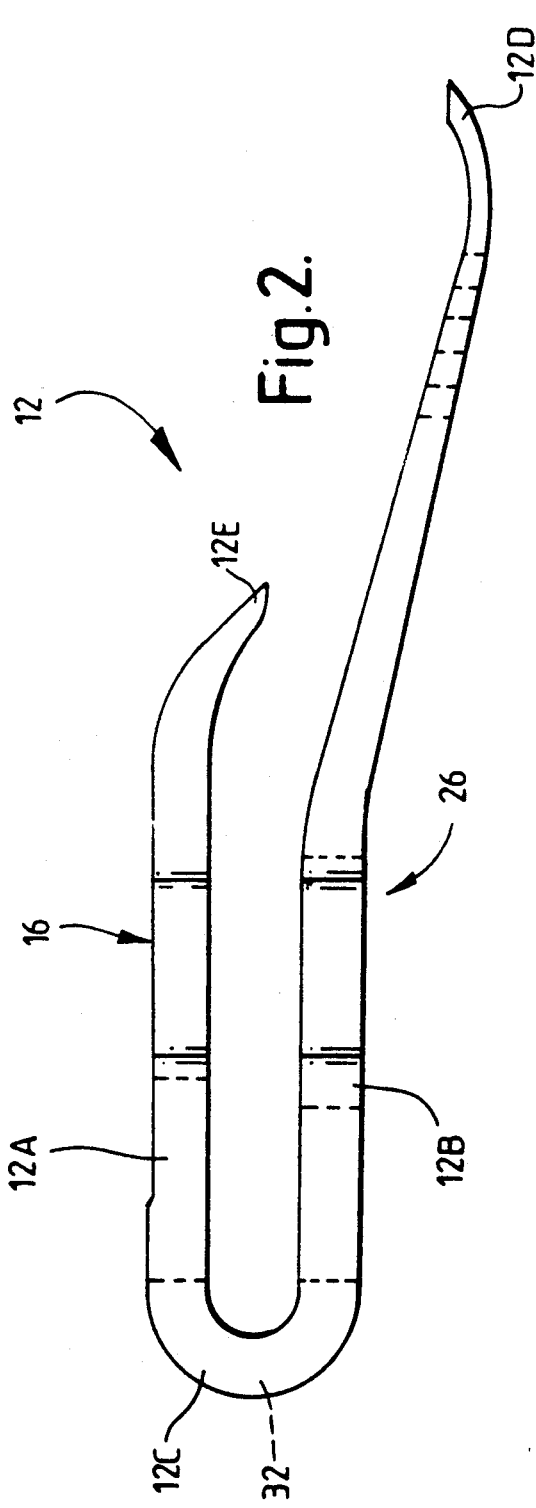
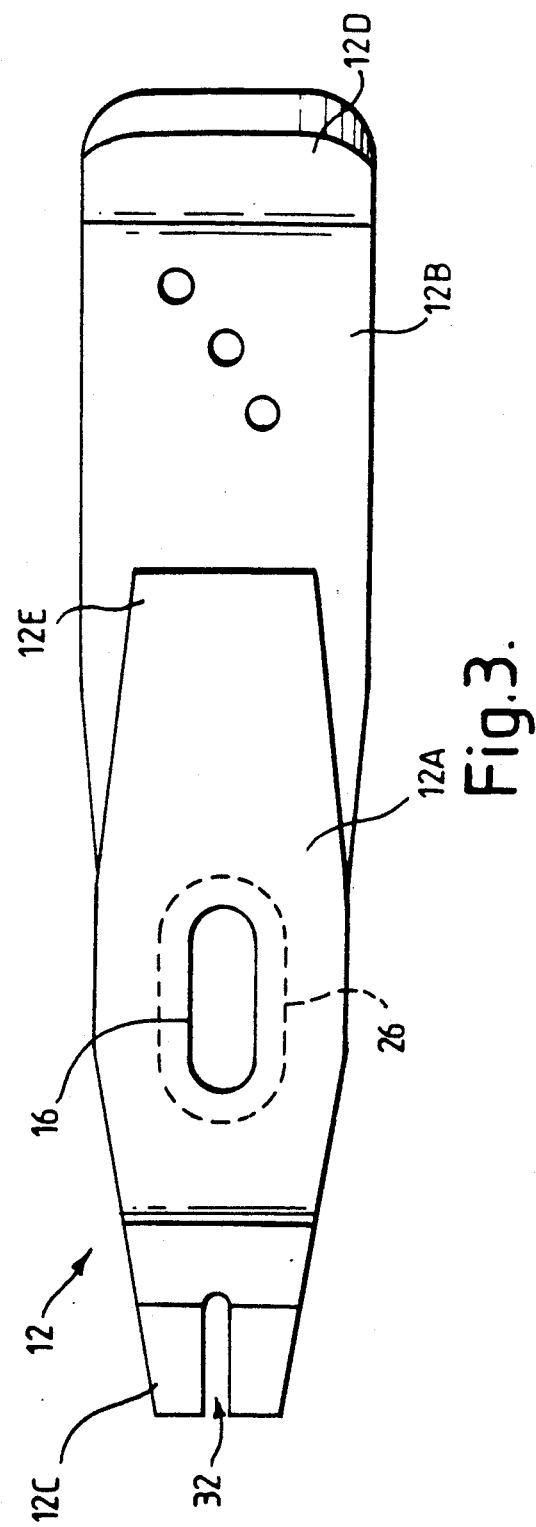

LOWELIMB PROTHESIS

This invention relates to a lower limb prosthesis and to an artificial foot.

It is well known that an artificial foot can be provided with an energy storing resilient element to assist an amputee in obtaining a natural and comfortable gait and, in the case of the relatively active amputee, in running. In one known arrangement, the resilient element comprises a resilient elongate keel in the form of a cantilever extending forwardly from an integral upper connecting member having an interface for connection to an ankle or shin member. To achieve a required degree of dorsi-flexion under load the cantilever portion is joined by an integral resilient heel portion to the upper member at a position adjacent the heel of the foot. As the patient transfers weight following heel contact, the keel flexes, storing potential energy which is then converted into kinetic energy on "push-off". Such feet have limitations for walking.

According to a first aspect of this invention, a lower limb prosthesis comprises: an energy storing foot which is resiliently deformable to allow dorsi flexion of an anterior portion of the foot relative to an ankle mounting portion of the foot; and a resilient ankle joint coupling the ankle mounting portion of the foot to an upper component of the prosthesis and arranged to allow plantar movement of the foot from a rest position relative to the upper component but substantially to prevent dorsi movement of the foot from the rest position.

By combining a flexible ankle joint with an energy storing foot in this manner, the walking characteristics associated with prior limbs with energy storing feet are much improved upon, the limitation of dorsi-flexion in the ankle joint allowing use of the energy storing property of the foot for aiding "push-off" during the walking or running cycle.

The maximum angle of dorsi-flexion is considerably less than the maximum angle of plantar flexion, and may be less than 5° or, preferably, less than 3°. Of the total dorsi-flexion of the assembly of the foot and the ankle joint, the contribution due to the ankle joint over the majority of the range of the total dorsi-flexion is normally less than 30 per cent. In contrast, of the total plantar flexion of the combination of the foot and the ankle joint, over the majority of the total plantar flexion range, the plantar flexion contribution due the ankle joint preferably exceeds 85 per cent of the total. Generally the rate of resistance of the joint to dorsi-flexion is at least ten times that for plantar flexion in terms of angular deflection per unit moment applied.

Improved walking characteristics can be obtained if the ankle joint is able to execute not only plantar flexion, but also medial and lateral flexion. Such flexion properties may be obtained by constructing the ankle joint as a ball and socket joint and by fitting a resilient ring around the shank or the ball member of the ball and socket joint, and by arranging for the socket portion of the joint to extend around the shank outside the ring in the form of a skirt. When the ankle joint is flexed, the ring is compressed between the skirt and the ball member shank to resist flexion. The skirt may be arranged so as to engage the ring only by the resistance of the ball and socket joint itself, while medial, lateral and dorsi-flexion are additionally resisted by the ring. To virtually prevent dorsi-flexion of the ankle joint, the ring may have one or more stiffening elements embedded in its anterior portion.

Alternatively, stop surfaces may be provided on the upper prosthesis component and the foot on the anterior side of the joint, these surfaces being arranged to engage one another in dorsi-flexion. A further alternative is the provision of strap means between the upper prosthesis component and the foot on the posterior side of the joint, the strap means being of a length such that it is tensioned in dorsi-flexion, thereby substantially to prevent further dorsi-flexion.

The invention also includes, according to a second aspect thereof, an artificial foot comprising a keel having an upper load receiving portion, an elongate resiliently deflectable lower portion arranged longitudinally of the foot for transmitting applied loads to the sole of the foot, and a posterior connection connecting the lower portion to the upper portion in a heel portion of the foot, and further comprising a longitudinally adjustable support member coupling the upper portion and the lower portion ahead of the posterior connection to provide a fulcrum for the lower portion at a position which is variable longitudinally of the foot thereby to allow adjustment of the resilience of the foot. Such a foot allows the degree of dorsi-flexion for a given load to be varied according the type of use required by the patient and according the weight of the patient.

A particularly simple and effective keel construction which may be adopted is a resilient single-piece fibre-reinforced plastics strip U-shaped in side elevation, with the lower keel portion extending from the heel portion of the foot into the region of the ball of the foot. The adjustable support member may be a bar extending transversely of the foot between an upper surface of the lower keel portion and a lower surface of the upper keel portion, the bar being located by a longitudinal bolt passing through an aperture in the posterior connection of the keel to be accessible at the rear of the foot.

The upper portion of the endoskeletal structure may extend forwardly of an ankle or shin connection, its anterior end acting as a stop to support the lower keel portion during severe dorsi-loading.

The foot may be connected to an ankle joint or directly to a shin member forming part of the prothesis and may be detachable from or integral with parts of the ankle joint and/or shin member.

The invention will now be described by way of example with reference to the drawings in which:

FIG. 2 is a side elevation of a keel for a foot forming part of the prosthesis of FIG. 1;

FIG. 3 is a plan view of the keel;

Figure 1:
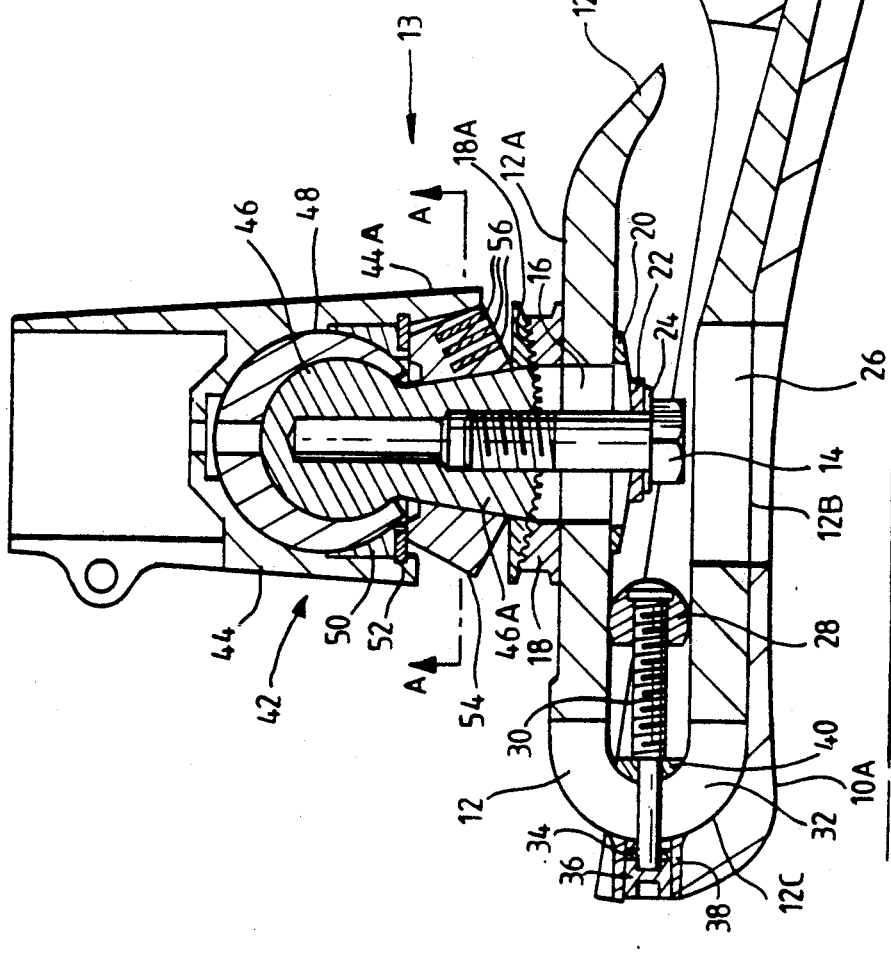
FIG. 1 is a vertical cross-section of a lower limb prosthesis in accordance with the invention, viewed from one side.

Referring to FIGS. 1 to 3, a lower limb prosthesis in accordance with the invention includes a foot 10 with an endoskeletal structure comprising a single-piece keel 12 having an upper plate portion 12A for mounting an ankle joint 13 and for receiving loads through the ankle joint, and an integral elongate lower portion 12B in the form of a strip running lengthwise of the foot for transmitting the loads to the sole of the foot. The upper and lower keel portions 12A and 12B are joined together at their posterior ends adjacent the heel 10A of the foot by an integral curved connecting portion 12C so that the three portions 12A, 12B and 12C of the keel constitute a U-shaped section in side elevation, in the form of a folded strip.

The lower keel portion 12B is parallel-sided in its anterior region and terminates in the region of the ball of the foot in an upwardly directed lip 12D. Its thickness increases in the posterior direction, while the width narrows to a minimum in the connecting portion 12C. The upper plate portion 12A is generally wider than the connecting portion and tapers forwardly to a downwardly inclined stop portion 12E which serves to limit dorsi-flexion of the keel 12B to a predetermined angle. The lower keel portion 12B is seated in a moulded flexible polyurethane foam cosmesis 10B corresponding approximately in shape to the shape of the natural foot.

Attachment of the upper keel portion 12A to the ankle joint 13 is achieved by means of a vertical bolt 14 which passes through an oval aperture 16 in the upper portion 12A and is threaded in the joint 13 (FIG. 1). Washers 18 and 20 are placed above and below the upper keel portion 12A to allow adjustment of the foot angle in effect a heel height adjustment), the upper washer 18 having a serrated concave cylindrical surface 18A for mating with a corresponding convex surface on the ankle joint 13, and the lower washer 20 having a coaxial convex lower surface to allow proper seating of the head of the bolt across the range of adjustment. Packing washers 22 and 24 are provided between the head of the bolt 14 and the convex washer 20. Access to the bolt head is gained via a second oval aperture 26 in the lower keel portion 12B and in the cosmesis 10B.

The effective length of the spring formed by the lower keel portion 12B is adjustable by means of a support member 28 which couples the upper portion 12A to the lower portion 12B by engaging the lower and upper surfaces respectively of these members ahead of the posterior connecting portion 12C. The support member 28 comprises a transversely arranged aluminium alloy bar having a threaded central hole bored across it to receive a longitudinally positioned adjusting screw 30. The screw 30 passes through a slot 32 (see FIG. 3) cut in the connecting portion 12C of the keel to emerge on the posterior face of the keel where it is attached by means of a cross pin 34 to an adjuster head 36 having a hexagon socket to suit an Allen key. Location of the screw 30 in the slot 32 is performed by a collar 38 bonded to the posterior face of the connecting portion 12C and a bored insert 40 fitted in the concave anterior surface of the connecting portion. The screw 30 is accessible at the heel of the foot where it can be rotated by a prosthetist or the patient so as to vary the position of the fulcrum formed by the bar 28.

It will be appreciated that this allows the stiffness of the keel to be adjusted to suit the weight of the patient and his or her level of activity, thereby reducing the range of keels that need to be provided to suit patients of different sizes, weights, and activities. It is even possible for patients themselves to alter the keel stiffness temporarily to suit a particular activity.

To achieve good walking characteristics, the artificial foot 10 described above is combined with an ankle joint 13 allowing plantar ankle flexion and medial/lateral flexion by allowing only restricted dorsi-flexion. Preferably, dosi-flexion is substantially eliminated. Such a combination allows the benefits of ankle flexion to be retained together with the ability to store energy in the keel of the foot during the period immediately prior to "push-off" in the walking or running cycle.

Figure 4:
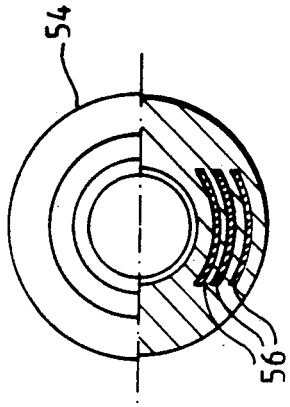
FIG. 4 is a partly sectioned plan view of a snubber ring forming part of an ankle joint of the prosthesis of FIG. 1, the section corresponding to the line A—A in FIG. 1.

Referring to FIGS. 1 and 4, an example of an ankle joint 13 having the required flexion characteristics is in the form of a ball and socket joint 42. The joint 42 has a socket member formed by an upper limb component which, in this example, is the lower end portion 44 of a shin member. The socket member 44 houses a ball member 46 bolted to the upper portion 12A of the keel 12. A resilient part-spherical cover 48 is fitted over the ball member 46, the assembly of the ball member 46 and the cover 48 being clamped in the socket member 44 by an integral ring 50 held in position by an expanding circlip 52 housed in a groove in the shin member end portion 44.

The shin member end portion 44 has a depending skirt 44A extending around and spaced from a connection shank 46A of the ball member 46. Between the skirt 44A and the shank 46A is a resilient snubber ring 54. The skirt 44A overlies only the medial, anterior and lateral outer faces of the snubber ring 54 thereby restricting medial, dorsi- and lateral flexion of the ankle joint, the plantar flexion allowed by the ball and socket joint being largely unaffected. To further restrict dorsi-flexion, the snubber ring 54 has encapsulated within its anterior portion a plurality of stiffening plates 56 which serve to restrict the resilience of the snubber ring in its anterior portion so as to increase further the resistance of the ankle joint to dorsi-flexion. Each plate 56 comprises an elongate rigid metal strip curved about an axis parallel to its surfaces and its end, and each is positioned transversely in the snubber ring 54 with its surfaces generally parallel to the outer part-conical surface of the ring 54. Restriction of dorsi-flexion is brought about not so much as a result of the presence of less rubber material in the anterior portion of the ring than in the medial or lateral portions, but rather by virtue of the limitation of the upward, downward and transverse deformation of the rubber material caused by the plates and their adhesion to the rubber material.

The ankle joint described above is a development of a joint disclosed in British Patent Specification No. 2161390A, the content of which is incorporated in this specification by reference.

Other means of restricting dorsi-flexion of the ankle joint may be employed. For instance, the plates 56 may be replaced by a single block of rigid material embedded in and/or bonded to the snubber ring. Alternatively, the skirt 44A may be extended to abut the keel upper portion 12A or parts coupled to that portion or to the ball member 46. Yet a further possibility is the provision of a flexible strap on the posterior side of the ankle joint, joining the shin member end portion 44 to the keel upper portion. Indeed, a combination of more than one of the three techniques described above may be used.

The effect of the stiffening plates 56 is substantially to prevent dorsi-flexion. Some initial dorsi movement of the foot will be taken up by the joint 13, but this is limited to less than 3°, and over the majority of the range of combined dorsi-flexion of the foot 10 and the joint 13, the dorsi-flexion due to flexion of the joint 13 is less than 30 percent of the total. In contrast the joint 13 presents comparatively little resistance to plantar flexion, to the extent that the flexion of the joint 13 during the range of combined plantar flexion of the joint 13 and the foot 10 represents at least 85 per cent of the total. These properties are illustrated in FIGS. 5 and 6.

Figure 5:
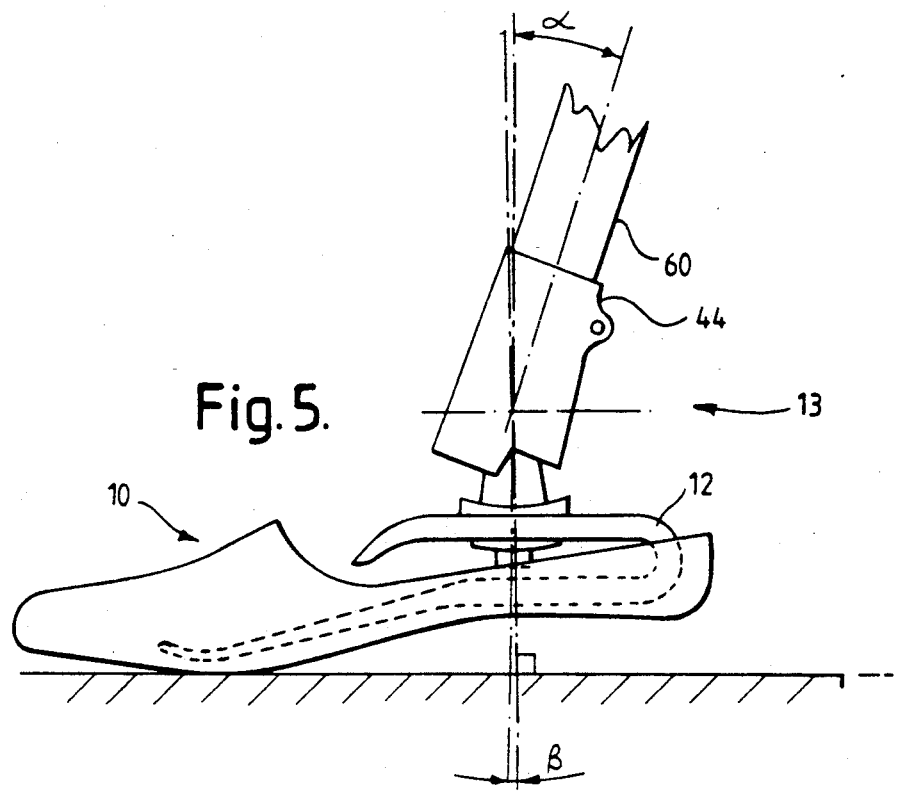
FIG. 5 is a diagrammatic side elevation of a prosthesis in accordance with the invention, shown in a plantar-flexed condition.

Referring to FIG. 5, when the combination of a downward force along the shin axis and a plantar moment about the ankle joint axis is applied to a shin tube 60 mounted in the upper component 44, the ankle joint 13 executes plantar flexion, as shown, by an angle $\alpha$. The keel 12 also contributes to the total plantar flexion of the arrangement, producing a further flexion of angle $\beta$. However, the rate of resilience of the ankle joint 13 is such that the angle $\alpha$ is greater than or equal to 0.85 $(\alpha+\beta)$. These angles can be measured by measuring the deviation of the shin tube axis from a rest position corresponding to the state of the foot and ankle joint when no external load is applied, to a flexed position when the force and moment referred to above are applied. The required combination of downward force and posterior moment may be produced for test purposes by holding the foot 10 in a nest or cradle (not shown) with the shin axis perpendicular to a ground plane (typically, the lower surface of the heel of the foot is 15 mm above the ground plane with the sole in the region of the ball of the foot touching the plane) and then applying a vertically downwardly directed load on a bracket (not shown) rigidly attached to the shin tube 60, the length and position of the bracket being such that the load acts through a point 60 mm behind the shin axis and 150 mm above the axis of rotation of the ankle joint 13.

Figure 6:
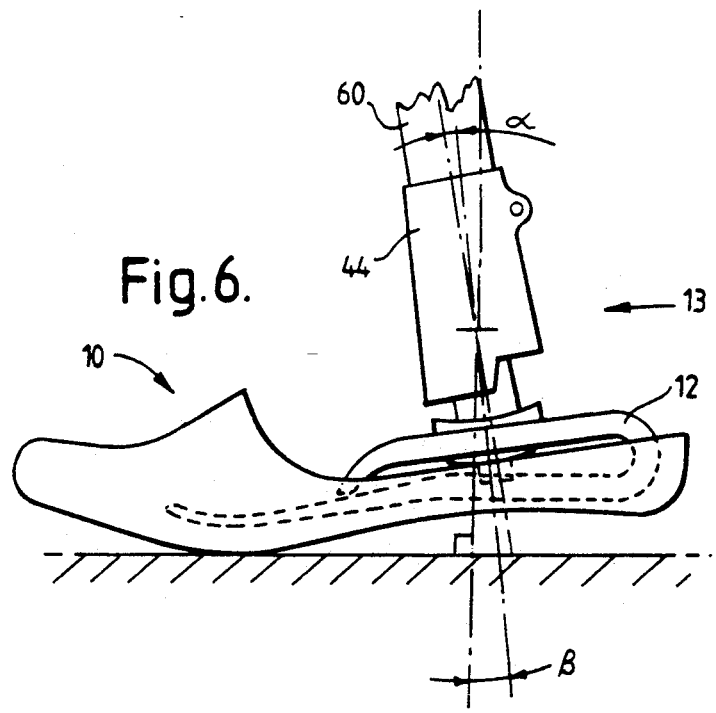
FIG. 6 is an elevation corresponding to that of FIG. 5, showing the prosthesis in a dorsi-flexed condition.

Similarly, referring to FIG. 6, the dorsi-flexion characteristics can be measured by applying a downward force along the shin axis and a dorsi moment about the ankle axis to the shin tube 60.

In this case, the shin tube 60 executes an anti-clockwise movement as seen in FIG. 6, the ankle joint 13 and the keel 12 again contributing to the flexion by angles $\alpha$ and $\beta$ respectively. However, in this case, due to the relative stiffness of the ankle joint 13 in dorsi-flexion, $\alpha$ is less than or equal to 0.3 $(\alpha+\beta)$. The required downward force and dorsi moment may be produced for test purposes by, again, holding the foot 10 in a nest or cradle so that the heel and ball of the foot remain substantially fixed in position relative to the ground plane, and applying a vertically downwardly directed load on a bracket (not shown) rigidly attached to the shin tube 60, the length and position of the bracket being such that the load acts through a point 100 mm to the anterior of the shin tube 60 and 150 mm above the ankle joint axis of rotation.

We claim:

1. A lower limb prosthesis comprising:
   an energy storing foot having an anterior portion, an ankle mounting portion, and an internal energy storing keel member which extends from said ankle mounting portion to said anterior portion and which, between said portions has lengthwise-distributed resilience in the metatarsal region of the foot, whereby the keel member is resiliently deformable to allow dorsi movement of the anterior portion relative to the ankle mounting portion; and
   a resilient ankle joint for coupling the ankle mounting portion of the foot to an upper component of the prosthesis, the ankle joint including means for allowing plantar movement of the ankle mounting portion of the foot from a rest position relative to the upper component but substantially preventing dorsi movement of the ankle mounting portion of the foot from the rest position relative to the upper component, whereby at least the majority of the dorsi-flexion of the combination of the foot and the ankle joint occurs in the keel member.

2. A prosthesis according to claim 1, wherein the ankle joint is arranged such that the maximum dorsi-flexion of the ankle joint is less than or equal to 3°.

3. A prosthesis according to claim 1, wherein the foot and the ankle joint are so arranged that over the majority of the range of combined dorsi-flexion of the foot and the ankle joint, the flexion of the ankle joint represents not more than 30% of the combined dorsi-flexion.

4. A prosthesis according to claim 1, wherein the upper component defines a shin axis of the prosthesis and wherein the ankle joint and the foot are so constructed that, over the majority of the range of the combined dorsi-flexion of the foot and the ankle joint, the dorsi-flexion of the ankle joint represents not more than 30% of the said combined dorsi-flexion when the upper component is loaded by the combination of a force directed downwardly along the shin axis and a dorsi moment about the ankle joint, the loading being equivalent to the application of a vertically and downwardly directed force on an anterior extension of the upper component such that the force is applied at a distance of 100 mm to the anterior of the shin axis and at a height of 150 mm above an axis of rotation defined by the ankle joint.

5. A prosthesis according to claim 1, wherein the upper component defines a shin axis, wherein the foot is so constructed to allow plantar movement of the foot anterior portion relative to the ankle joint mounting portion, and wherein the foot and ankle joint are so constructed that over the majority of the range of combined plantar movement of the foot and the ankle joint, the plantar movement due to the ankle joint represents at least 85% of the said combined plantar movement when the upper component is loaded by the combination of a force directed downwardly along the shin axis and a plantar moment about the ankle joint, the loading being equivalent to the application of a vertically and downwardly directed force on a posterior extension of the upper component such that the force is applied at a distance of 60 mm to the posterior of the shin axis and at a height of 150 mm about an axis of rotation defined by the ankle joint.

6. A lower limb prosthesis comprising:
   an energy storing foot having an anterior portion, an ankle mounting portion and an internal energy storing keel member which extends from said ankle mounting portion to said anterior portion and which, between said portions has a lengthwise-distributed resilience in the metatarsal region of the foot, whereby, the keel member is resiliently deformable to allow dorsi movement of the anterior portion relative to the ankle mounting portion; and
   a resilient ankle joint for coupling the ankle mounting portion of the foot to an upper component of the prosthesis and arranged to allow plantar movement of the ankle mounting portion of the foot from a rest position relative to the upper component but substantially to prevent dorsi movement of the ankle mounting portion of the foot from the rest position relative to the upper component, whereby at least the majority of the dorsi-flexion of the combination of the foot and ankle joint occurs in the keel member and wherein the ankle joint is constructed so as to allow medial and lateral flexion.

7. A prosthesis according to claim 6, wherein the ankle joint comprises a ball and socket joint.

8. A prosthesis according to claim 7, wherein the ball and socket joint has a ball member comprising a ball portion and a connection shank, and a socket member surrounding the ball portion and having an extension in registry with but spaced radially from the shank, and wherein the ankle joint further comprises a resilient ring encircling the shank and located between the extension and the shank, the arrangement of the extension being such that the ring acts as a resilient buffer resisting at least medial and lateral flexion of the ankle joint.

9. A prosthesis according to claim 8, wherein the extension is constructed to engage the ring only on the anterior, medial and lateral faces thereof, and wherein the ring has at least one stiffening element embedded in an anterior portion thereof for substantially preventing dorsi-flexion of the ankle joint whilst permitting medial, lateral and plantar flexion.

10. A prosthesis according to claim 1, wherein the internal keel member comprises a leaf spring extending into the anterior portion of the foot.

11. A prosthesis according to claim 10, wherein the ankle mounting portion of the foot is integral with the leaf spring, the combination of the ankle mounting portion and the leaf spring being formed of a fiber-reinforced plastics material.

12. A prosthesis according to claim 1, wherein the keel member comprises an elongate lower keel portion extending lengthwise in the foot from a heel portion of the foot into the said anterior portion, and a posterior connecting portion connecting the ankle mounting portion to the lower keel portion in the heel portion of the foot.

13. A prosthesis according to claim 12, wherein the foot further comprises an adjustable support member coupling the ankle mounting portion and the lower keel portion thereof ahead of the posterior connecting portion to provide a fulcrum for the lower portion at a position which is variable longitudinally of the foot.

14. A prosthesis according to claim 13, wherein the ankle mounting portion and the keel member are formed as a single-piece resilient fiber-reinforced plastics strip U-shaped in side elevation, the ankle mounting portion comprising a plate connectable to the ankle joint.

15. A prosthesis according to claim 14, wherein the adjustable support member comprises a bar extending transversely of the foot between an upper surface of the lower keel portion and a lower surface of the ankle mounting portion.

16. A prosthesis according to claim 15, wherein the bar is attached to a longitudinally extending bolt passing through an aperture in the posterior connecting portion of the keel member.

17. A lower limb prosthesis comprising:
an energy storing foot having an anterior portion, an ankle mounting portion, and an internal energy storing keel member which extends from said ankle mounting portion to said anterior portion and which between said portions has lengthwise-distributed resilience in the metatarsal region of the foot, whereby, the keel member is resiliently deformable to allow dorsi movement of the anterior portion relative to the ankle mounting portion; and a resilient ankle joint for coupling the ankle mounting portion of the foot to an upper component of the prosthesis and arranged to allow plantar movement of the ankle mounting portion of the foot from a rest position relative to the upper component but substantially to prevent dorsi movement of the ankle mounting portion of the foot from the rest position relative to the upper component, whereby at least the majority of the dorsi-flexion of the combination of the foot and the ankle joint occurs in the keel member and wherein the ankle joint has a lower member detachably connected to the ankle mounting portion of the foot, and wherein the relative position of the said lower member and the ankle mounting portion can be set to any of a plurality of different positions for setting a required heel height.

18. A prosthesis according to claim 1, wherein the ankle joint is constructed so as to restrict dorsi-flexion of the joint to an angle less than or equal to 5°.

19. A prosthesis according to claim 1, wherein the rate of resilience of the ankle joint for plantar movement is greater than ten times that for dorsi movement, the resilience being measured as the angular deflection per unit moment applied.

20. An energy storing artificial foot comprising a keel having an upper load receiving portion, an elongate resiliently deflectable lower portion arranged longitudinally of the foot for transmitting applied loads to the sole of the foot, and a posterior connection connecting the lower portion to the upper portion in a heel portion of the foot, and further comprising a longitudinally adjustable support member coupling the upper portion to the lower portion ahead of the posterior connection to provide a fulcrum for the lower portion at a position which is variable longitudinally of the foot thereby to allow adjustment of the resilience of the foot.

21. An artificial foot according to claim 20, wherein the keel is a resilient single-piece fibre-reinforced plastics strip U-shaped in side elevation, with the lower portion extending from the heel portion of the foot into the region of the ball of the foot.

22. An artificial foot according to claim 20, wherein the adjustable support member comprises a bar extending transversely of the foot between an upper surface of the lower keel portion and a lower surface of an upper keel portion, the bar being located by a longitudinal bolt passing through an aperture in the said posterior connection of the keel to be accessible at the rear of the foot.

23. A lower limb prosthesis comprising:
an energy storing foot having an anterior portion and an ankle mounting portion and an elongate resilient internal keel portion in the form of a leaf spring extending longitudinally of the foot in the metatarsal region and into the anterior portion whereby the anterior portion is capable of executing dorsi movement with respect to the ankle mounting portion; and a resilient ankle joint for coupling the ankle mounting portion of the foot to an upper component of the prosthesis and arranged to allow plantar movement of the ankle mounting portion of the foot from a rest position relative to the upper component but substantially to prevent dorsi movement of the ankle mounting portion of the foot from the rest position relative to said upper component whereby at least the majority of the dorsi-flexion of the combination of the foot and the ankle joint occurs in the keel.

24. A prosthesis according to claim 23, wherein the ankle joint is arranged such that the maximum dorsi-flexion of the ankle joint is less than or equal to 3°.

25. A prosthesis according to claim 23, wherein the foot and the ankle joint are so arranged that over the majority of the range of combined dorsi-flexion of the foot and the ankle joint, the flexion of the ankle represents not more than 30% of the combined dorsi-flexion.

26. A prosthesis according to claim 23, wherein the ankle joint is constructed so as to allow medial and lateral flexion.

27. A prosthesis according to claim 23, wherein the ankle joint comprises a ball and socket joint having a ball member comprising a ball portion and a connection shank, and a socket member surrounding the ball portion and having an extension in registry with but spaced radially from the shank, the ankle joint further comprising a buffer located between the extension and the connection shank for substantially preventing relative approaching movement of the extension with respect to the shank thereby substantially to prevent dorsi-flexion of the ankle joint.

* * * * *